US007112581B2

(12) United States Patent
Mitchell et al.

(10) Patent No.: US 7,112,581 B2
(45) Date of Patent: Sep. 26, 2006

(54) MACROCYCLIC LACTAMS

(75) Inventors: Scott C. Mitchell, San Diego, CA (US); Benjamin Nicholson, San Diego, CA (US)

(73) Assignee: Nereus Pharmaceuticals, Inc., San Diego, CA (US)

( * ) Notice: Subject to any disclaimer, the term of this patent is extended or adjusted under 35 U.S.C. 154(b) by 141 days.

(21) Appl. No.: 10/673,036

(22) Filed: Sep. 25, 2003

(65) Prior Publication Data

US 2004/0132997 A1    Jul. 8, 2004

Related U.S. Application Data

(60) Provisional application No. 60/414,817, filed on Sep. 27, 2002.

(51) Int. Cl.
*A61K 31/395*    (2006.01)
*A61K 35/02*     (2006.01)
*A61P 35/00*     (2006.01)
*C07D 225/02*    (2006.01)

(52) U.S. Cl. ..................................... 514/183; 540/463
(58) Field of Classification Search ................ 540/463; 514/183
See application file for complete search history.

(56) References Cited

U.S. PATENT DOCUMENTS

| | | | |
|---|---|---|---|
| 5,445,829 A | 8/1995 | Paradissis et al. |
| 5,565,561 A | 10/1996 | Müller et al. |
| 5,576,012 A | 11/1996 | Baver et al. |
| 5,601,845 A | 2/1997 | Buxton et al. |
| 5,641,515 A | 6/1997 | Ramtoola |
| 5,653,987 A | 8/1997 | Modi et al. |
| 5,654,286 A | 8/1997 | Hostetler |
| 5,667,809 A | 9/1997 | Trevino et al. |
| 5,683,676 A | 11/1997 | Akehurst et al. |
| 5,688,529 A | 11/1997 | Lidgate et al. |
| 5,707,615 A | 1/1998 | Cardin et al. |
| 5,707,641 A | 1/1998 | Gertner et al. |
| 5,726,181 A | 3/1998 | Hausheer et al. |
| 5,733,888 A | 3/1998 | Carver et al. |
| 5,874,443 A | 2/1999 | Kiely et al. |
| 5,886,210 A | 3/1999 | Rayle et al. |
| 5,992,683 A | 11/1999 | Sigl |
| 6,350,759 B1 | 2/2002 | Casara et al. |
| 6,500,825 B1 | 12/2002 | Lan et al. |
| 6,506,787 B1 | 1/2003 | Fujishita et al. |
| 6,509,331 B1 | 1/2003 | Audia et al. |

FOREIGN PATENT DOCUMENTS

WO    WO 99/07692    2/1999

WO    WO 00/37473    6/2000

OTHER PUBLICATIONS

Faulkner, D. John, "*Marine Pharmacology*", Antonie van Leeuwnhoek, vol. 77, pp. 135-145 (2000).
Fenical, William, et al., "*Marine Microorganisms as a Developing Resource for Drug Discovery*", Pharmaceutical News, vol. 9, pp. 489-494 (2002).
Gerber, Nancy N., "*A New Prodiginine (Prodigiosin-like) Pigment from Streptomyces. Antimalarial Activity of Several Prodiginines*", The Journal of Antibiotics, vol. XXVIII, No. 3, pp. 194-199 (Mar., 1975).
Kojiri, Katsuhisa, et al., "*A New Macrocyclic Lactam Antiobiotic, VE-14106, I. Taxonomy, Isolation, Biological Activity and Structural Elucidation*", The Journal of Antibiotics, vol. 45, No. 6, pp. 868-874 (Jun. 1992).
Okami, Yoshiro, "*The Search for Bioactive Metabolites from Marine Bacteria*", The Journal of Marine Biotechnology, vol. 1, pp. 59-65 (1993).
Shindo, Kazutoshi, et al., "*Vicenistatin, a Novel 20-Membered Macrocyclic Lactam Antitumor Antibiotic*", The Journalo of Antibiotics, vol. 46, No. 7, pp. 1076-1081.
Takahashi, I., et al., "*Communication to the Editor*", The Journal of Antibiotics, vol. 50, No. 2, 186-188.
Wasserman, Harry H., et al., Journal of the American Chemical Society; vol. 91, No. 5, pp. 1263-1264 (Feb. 1969).

(Continued)

Primary Examiner—Bruck Kifle
(74) Attorney, Agent, or Firm—Knobbe, Martens, Olson & Bear, LLP

(57) ABSTRACT

Compounds represented by the following structure (I), acid-addition salts and pro-drugs are disclosed:

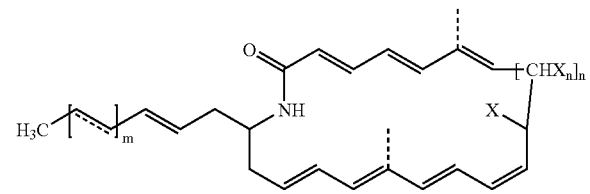

wherein the ring structure includes no substitutions, one substitution, or more than one substitution; and wherein n is equal to an integer grater than 1, preferably 2, 3, or 4; m is equal to a positive integer, preferably 1, 2 or 3, and each separate $X_n$ and X are each separately selected from a nucleophilic residue, preferably —H, —OH, —O—CO-alkyl, —O-alkyl, —NH$_2$, a halogen and the like; and wherein the dashed line represents a C—C bond or a C—H bond, and the dashed and solid line represents either a carbon-carbon single bond or a carbon-carbon double bond.

18 Claims, 5 Drawing Sheets

OTHER PUBLICATIONS

Arai, et al. "Absolute Stereochemistry of Vicenistatin, a Novel 20-Membered Macrocyclic Lactam Antitumor Antibiotic." *Tetrahedron Letters*. 39: 3181-3184 (1998).

International Search Report for International Application No. PCT/US 03/30518 dated May 25, 2004.

Alm, et al. "Effects of topically Applied $PGF_{2\alpha}$ and its Isopropylester on Normal and Glaucomatous Human Eyes." *Prog. Coin. Biol. Res.* 312:447-58 (1998).

"Bioreversible Carriers in Drug Design: Theory and Application," edited by E. B. Roche, Pergamon Press: New York, 14-21 (1987).

Fenical, William. "Chemical Studies of Marine Bacteria: Developing a New Resource." *Chem. Rev.* 93:1673-1683 (1993).

Fingl, et al. Basis of Therapeutics. 5th Edition. Macmillan Publishing Co. Chp. 13. "Drugs Effective in the Therapy of the Epilepsies," (1975).

Fingl, et al. Basis of Therapeutics. 5th Edition. Macmillan Publishing Co. Chp. 17. "Analgesic-Antipyretics, Anti-Inflammatory Agents, and Drugs Employed in the Therapy of Gout," (1975).

Fingl, Edward. Basis of Therapeutics. 5th Edition. Macmillan Publishing Co. Chp. 49. "Laxatives and Cathartics," (1975).

Higuchi, et al. "Pro-drugs as Novel Delivery Systems." A.C.S. Symposium Series, American Chemical Society. 14(3): 154-183 (1975).

Joshi, A. "Microparticulates for Ophthalmic Drug Delivery." *J. Ocul. Pharmacol.*, 10(1):29-45 (1994).

Khokhlova, et al. "A Chemical Study of the Major Vitamycin Component." Institute of Microbiology, Academy of Sciences of the USSR, Moscow, pp. 841-845, Russian (1964).

Krassilnikov, et al. "A New Species in the Group of Actinomyces Aurantiacus," pp. 482-489 (1960).

Mayer et al. "Efficacy of a Novel Hydrogel Formulation in Human Volunteers." *Ophthalmologica*. 210(2):101-3 (1996).

Mordenti, et al. "Intraocular Pharmacokinetics and Safety of a Humanized Monoclonal Antibody in Rabbits after Intravitreal Administration of a Solution or a PLGA Microsphere Formulation." *Toxicol. Sci.* 52(1):101-6 (1999).

Shedden, et al. "Efficacy and Tolerability of Timolol Maleate Ophthalmic Gel-Forming Solution Versus Timolol Ophthalmic Solution in Adults with Open-Angle Glaucoma or Ocular Hypertension: A Six-Month, Double-Masked, Multicenter Study." *Clin. Ther*, 23(3):440-50 (2001).

UV Spectrum of NPI3004 in Acetonitrile/$H_2O$

MACROCYCLIC LACTAMS

CROSS REFERENCE TO RELATED APPLICATIONS

This application claims priority under 35 U.S.C. § 119(e) to U.S. Provisional Application No. 60/414,817 filed Sep. 27, 2002, entitled "MACROCYCLIC LACTAMS," and which is incorporated herein by reference in its entirety.

BACKGROUND OF THE INVENTION

Field of the Invention

The present invention relates to compounds and methods for the synthetic and semi-synthetic preparation of such compounds in the fields of chemistry and medicine. More specifically, the present invention relates to compounds and procedures for making compounds useful in the treatment of diseases, including cancer. The compounds are also useful in the treatment of infectious disease.

SUMMARY OF THE INVENTION

Compounds, and methods for the synthetic and semi-synthetic preparation of such compounds, are disclosed for a class of compounds having the structure of Formula (I):

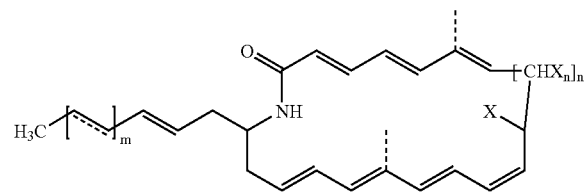

wherein the ring structure includes no substitutions, one substitution, or more than one substitution; and wherein n is equal to an integer greater than 1, preferably 2, 3, or 4; m is equal to a positive integer, preferably 1, 2 or 3, and each separate $X_n$ and X are each separately selected from a nucleophilic residue, preferably —H, —OH, —O—CO-alkyl, —O-alkyl, —NH$_2$, a halogen and the like; and wherein the dashed line represents a C—C bond or a C—H bond, and the dashed and solid line represents either a carbon-carbon single bond or a carbon-carbon double bond.

The disclosed compounds have the structure of the above Formula. The ring structure can be freely substituted according to techniques known to persons of skill in the art. In some embodiments the ring structure will include no substitutions, one substitution, or more than one substitution, for example, two or three substitutions. Hydrogen positions on the ring may be substituted with a lower alkyl, preferably a methyl group. For example, the ring structure may include no substitutions, one substitution, or more than one substitution. In certain embodiments the substitution will include the substitution of a hydrogen atom, a halogen atom, and saturated $C_1$–$C_{24}$ alkyl, unsaturated $C_1$–$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups, hydroxy, carboxy, —CO—O—R$_7$, cyano, halogenated alkyl including polyhalogenated alkyl, and carbonyl —CCO—R$_7$, wherein R$_7$ is selected from known moieties, preferably a hydrogen atom, a halogen atom, and saturated $C_1$–$C_{24}$ alkyl, unsaturated $C_1$–$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, or a substituted phenyl group. Also, the substitution can include the substitution of a lower alkyl.

In preferred embodiments, m can be equal to 0, 1, or 2, and preferably is 1. In other preferred embodiments, n is equal to 2, 3, or 4, and preferably is equal to 3. Further, in other preferred embodiments, each of X and $X_n$ is separately selected from preferably —H, —OH, —O—CO-alkyl, —O-alkyl, —NH$_2$, a halogen. Most preferably, X and $X_n$ is OH.

In a preferred embodiment the compound has the structure:

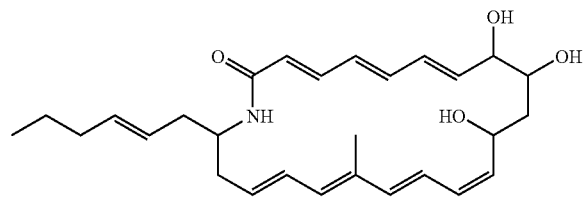

The methods of preparation of the compound as disclosed herein, may comprise the steps of obtaining and of purifying the above-compound as described in further detail herein. Semi-synthetic methods of derivitization are also disclosed and are known to those of skill in the art.

Other embodiments relate to treating an individual using the compounds disclosed herein and compositions comprising the compounds disclosed herein. It should be appreciated that by "compounds and compositions comprising the compound," is meant that the compounds may be in any suitable form for pharmaceutical delivery as discussed herein. For example, in some embodiments, the compounds or compositions comprising the same can include a pharmaceutically acceptable salt of the compound. The methods can include treating diseases such as cancer. In other embodiments the compounds can be used to treat infectious diseases. Disease is meant to be construed broadly to cover cancers and infectious diseases, and also autoimmune diseases, non infectious diseases and chronic conditions. The methods may include the steps of administering a compound or composition comprising the compound to an individual with a disease, such as cancer. For example, the cancer can be prostate, colon, leukemia, melanoma, and the like. Furthermore, the methods may include the steps of administering a compound or composition comprising the compound to an individual with an infectious disease. The infectious disease can be, for example, one caused by a enteric bacteria such as *E. coli*, one caused by *S. pneumoniae* or a *staphylococcus*, or one caused by *H. influenzae*, and the like. The compound or composition can be administered with a pharmaceutically acceptable carrier, diluent, excipient, and the like.

Other embodiments relate to methods of treating cancer that include the step of contacting a cancer cell with a compound of Formula (I). Still further embodiments relate to methods of treating cancer comprising contacting a patient diagnosed with cancer with a compound of Formula (I). In any of the embodiments the cancer can be, for example, prostate, colon, leukemia, melanoma, and the like.

BRIEF DESCRIPTION OF THE DRAWINGS

The accompanying drawings, which are incorporated in and form part of the specification, merely illustrate certain preferred embodiments of the present invention. Together with the remainder of the specification, they are meant to serve to explain preferred modes of making certain compounds of the invention to those of skilled in the art. In the drawings.

DETAILED DESCRIPTION OF PREFERRED EMBODIMENTS

Figure 1:
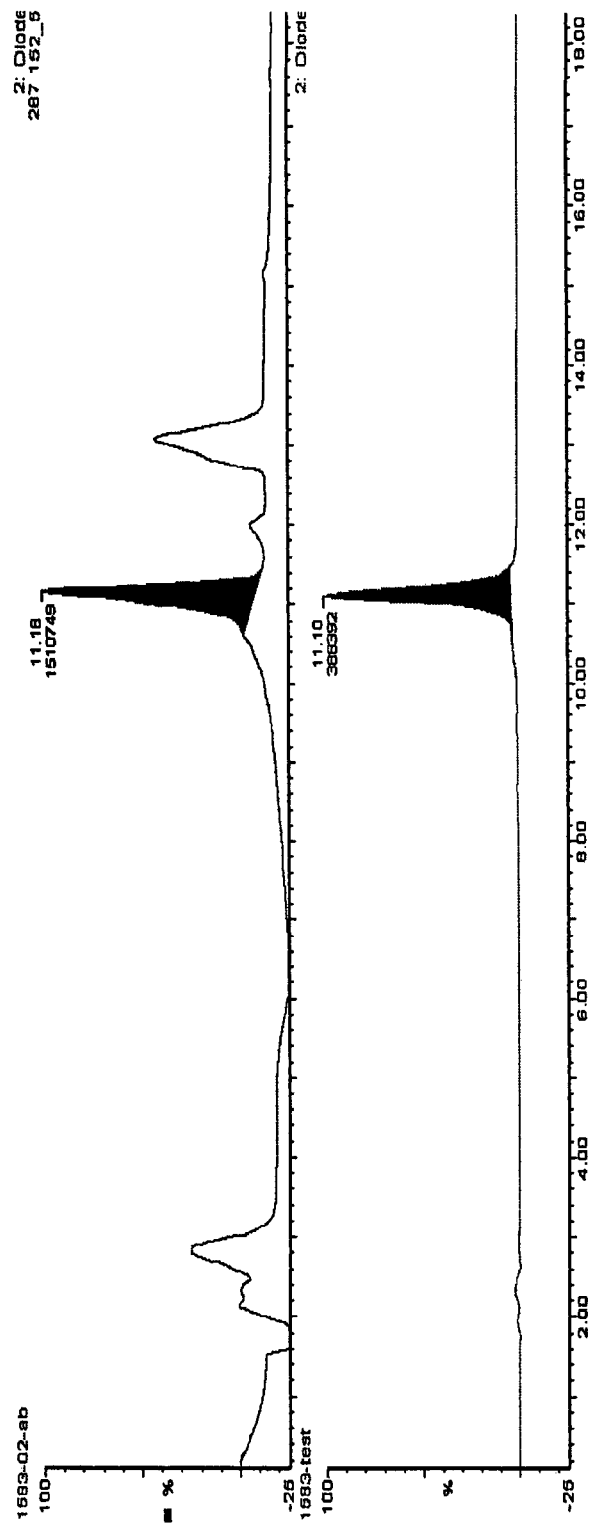
FIG. 1 depicts an HPLC chromatograph of the compound of the invention, showing its peak and other unrelated peaks.

Numerous references are cited herein. The references cited herein, including the U.S. patents cited herein, are to each be considered incorporated by reference in their entirety into this specification.

Embodiments of the invention include, but are not limited to providing a method for the preparation of compounds, including novel compounds, including macrocyclic lactams and analogs thereof, and to providing a method for producing pharmaceutically acceptable anti-tumor compositions, and anti-infectious disease compositions, for example. The methods can include the compositions in relatively high yield, wherein the compounds and/or their derivatives are among the active ingredients in these compositions. Other embodiments relate to providing novel compounds not obtainable by currently available methods. Furthermore, embodiments relate to methods of treating cancer and infectious diseases, particularly human cancer and human infectious diseases, comprising the step of administering an effective amount of a member of a class of new compounds. Preferred embodiments relate to the compounds and methods of making and using such compounds disclosed herein, but not necessarily in all embodiments of the present invention, these objectives are met.

The invention provides compounds, and methods of producing a class of compounds, wherein the compounds are represented by Formula (I):

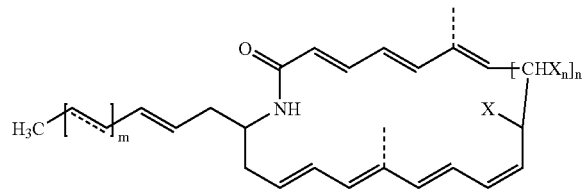

The disclosed compounds have the structure of the above Formula. The ring structure can be freely substituted according the skill in the art. Hydrogen positions on the ring can be substituted with a lower alkyl, preferably a methyl group. For example, the ring structure can include no substitutions, one substitution, more than one substitution, and the like. In some embodiments the substitution can include the substitution of a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, and substituted phenyl groups, hydroxy, carboxy, —CO—O—$R_7$, cyano, halogenated alkyl including polyhalogenated alkyl, and carbonyl —CCO—$R_7$, wherein $R_7$ is selected from a hydrogen atom, a halogen atom, and saturated $C_1$-$C_{24}$ alkyl, unsaturated $C_1$-$C_{24}$ alkenyl, cycloalkyl, cycloalkenyl, alkoxy, cycloalkoxy, aryl, substituted aryl, heteroaryl, substituted heteroaryl, amino, substituted amino, nitro, azido, substituted nitro, phenyl, substituted phenyl groups, and the like.

In some embodiments, the ring structure may includes no substitutions, one substitution, or more than one substitution. Furthermore, n may equal an integer greater than 1, preferably 2, 3, or 4, and more preferably is equal to 3. Also, m may be equal to a positive integer, preferably 1, 2 or 3, and more preferably is equal to 1. As a further example, each separate $X_n$ and X each may be separately selected from a nucleophilic residue, preferably —H, —OH, —O—CO-alkyl, —O-alkyl, —$NH_2$, a halogen and the like. Preferably, X and $X_n$ are OH. The dashed line may represent a C—C bond or a C—H bond, for example, and the dashed and solid line represents either a carbon-carbon single bond or a carbon-carbon double bond. Also, the substitution can include the substitution of a lower alkyl.

In preferred embodiments the compound has the structure:

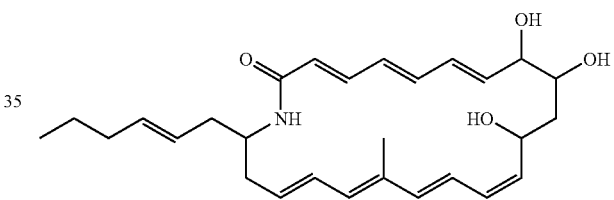

The disclosed compounds have the structure of the above formulas. The ring structure may be freely substituted according the skill in the art. Hydrogen positions on the ring can be substituted with a lower alkyl, preferably a methyl group.

The invention also provides pharmaceutically acceptable salts and pro-drug esters of the compound of Formulae (I) and provides methods of obtaining and purifying such compounds by the methods disclosed herein.

The term "pro-drug ester," especially when referring to a pro-drug ester of the compound of Formula (I) synthesized by the methods disclosed herein, refers to a chemical derivative of the compound that is rapidly transformed in vivo to yield the compound, for example, by hydrolysis in blood or inside tissues. The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl) methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14–21 (1987) (providing examples of esters useful as pro-drugs for compounds containing carboxyl groups). Each of the above-mentioned references is hereby incorporated by reference in its entirety.

The term "pro-drug ester," as used herein, also refers to a chemical derivative of the compound that is rapidly transformed in vivo to yield the compound, for example, by hydrolysis in blood. The term "pro-drug ester" refers to derivatives of the compounds disclosed herein formed by the addition of any of several ester-forming groups that are hydrolyzed under physiological conditions. Examples of pro-drug ester groups include pivoyloxymethyl, acetoxymethyl, phthalidyl, indanyl and methoxymethyl, as well as other such groups known in the art, including a (5-R-2-oxo-1,3-dioxolen-4-yl)methyl group. Other examples of pro-drug ester groups can be found in, for example, T. Higuchi and V. Stella, in "Pro-drugs as Novel Delivery Systems", Vol. 14, A.C.S. Symposium Series, American Chemical Society (1975); and "Bioreversible Carriers in Drug Design: Theory and Application", edited by E. B. Roche, Pergamon Press: New York, 14–21 (1987) (providing examples of esters useful as pro-drugs for compounds containing carboxyl groups); both of which are incorporated herein by reference in their entireties.

The term "pharmaceutically acceptable salt," as used herein, and particularly when referring to a pharmaceutically acceptable salt of a compound, including Formula (I), and Formula (I) as synthesized by the methods disclosed herein, refers to any pharmaceutically acceptable salts of a compound, and preferably refers to an acid addition salt of a compound. Preferred examples of pharmaceutically acceptable salt are the alkali metal salts (sodium or potassium), the alkaline earth metal salts (calcium or magnesium), or ammonium salts derived from ammonia or from pharmaceutically acceptable organic amines, for example $C_1$–$C_7$ alkylamine, cyclohexylamine, triethanolamine, ethylenediamine or tris-(hydroxymethyl)-aminomethane. With respect to compounds synthesized by the method of the invention that are basic amines, the preferred examples of pharmaceutically acceptable salts are acid addition salts of pharmaceutically acceptable inorganic or organic acids, for example, hydrohalic, sulfuric, phosphoric acid or aliphatic or aromatic carboxylic or sulfonic acid, for example acetic, succinic, lactic, malic, tartaric, citric, ascorbic, nicotinic, methanesulfonic, p-toluensulfonic or naphthalenesulfonic acid.

Preferred pharmaceutical compositions disclosed herein include pharmaceutically acceptable salts and pro-drug esters of the compound of Formula (I) obtained and purified by the methods disclosed herein. Accordingly, if the manufacture of pharmaceutical formulations involves intimate mixing of the pharmaceutical excipients and the active ingredient in its salt form, then it is preferred to use pharmaceutical excipients which are non-basic, that is, either acidic or neutral excipients.

The term "halogen atom," as used herein, means any one of the radio-stable atoms of column 7 of the Periodic Table of the Elements, i.e., fluorine, chlorine, bromine, or iodine, with fluorine and chlorine being preferred.

The term "alkyl," as used herein, means any unbranched or branched, substituted or unsubstituted, saturated hydrocarbon, with $C_1$–$C_6$ unbranched, saturated, unsubstituted hydrocarbons being preferred, with methyl, ethyl, isobutyl, and tert-butyl being most preferred. Among the substituted, saturated hydrocarbons, $C_1$–$C_6$ mono- and di- and per-halogen substituted saturated hydrocarbons and amino-substituted hydrocarbons are preferred, with perfluromethyl, perchloromethyl, perfluoro-tert-butyl, and perchloro-tert-butyl being the most preferred. The term "substituted" has its ordinary meaning, as found in numerous contemporary patents from the related art. See, for example, U.S. Pat. Nos. 6,509,331; 6,506,787; 6,500,825; 5,922,683; 5,886,210; 5,874,443; and 6,350,759; all of which are incorporated herein in their entireties by reference. Specifically, the definition of substituted is as broad as that provided in U.S. Pat. No. 6,509,331, which defines the term "substituted alkyl" such that it refers to an alkyl group, preferably of from 1 to 10 carbon atoms, having from 1 to 5 substituents, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyacylamino, cyano, halogen, hydroxyl, carboxyl, carboxylalkyl, keto, thioketo, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl. The other above-listed patents also provide standard definitions for the term "substituted" that are well-understood by those of skill in the art. The term "cycloalkyl" refers to any non-aromatic hydrocarbon ring, preferably having five to twelve atoms comprising the ring. The term "acyl" refers to alkyl or aryl groups derived from an oxoacid, with an acetyl group being preferred.

The term "alkenyl," as used herein, means any unbranched or branched, substituted or unsubstituted, unsaturated hydrocarbon including polyunsaturated hydrocarbons, with $C_1$–$C_6$ unbranched, mono-unsaturated and di-unsaturated, unsubstituted hydrocarbons being preferred, and mono-unsaturated, di-halogen substituted hydrocarbons being most preferred. In the $R_1$ and $R_4$ positions, of the compound of structure (I) a Z-isoprenyl moiety is particularly preferred. The term "cycloalkenyl" refers to any non-aromatic hydrocarbon ring, preferably having five to twelve atoms comprising the ring.

The terms "aryl," "substituted aryl," "heteroaryl," and "substituted heteroaryl," as used herein, refer to aromatic hydrocarbon rings, preferably having five, six, or seven atoms, and most preferably having six atoms comprising the ring. "Heteroaryl" and "substituted heteroaryl," refer to aromatic hydrocarbon rings in which at least one heteroatom, e.g., oxygen, sulfur, or nitrogen atom, is in the ring along with at least one carbon atom. The substituted aryls and heteroaryls can be substituted with any substituent, including those described above and those known in the art.

The term "alkoxy" refers to any unbranched, or branched, substituted or unsubstituted, saturated or unsaturated ether, with $C_1$–$C_6$ unbranched, saturated, unsubstituted ethers being preferred, with methoxy being preferred, and also with dimethyl, diethyl, methyl-isobutyl, and methyl-tert-butyl ethers also being preferred. The term "cycloalkoxy" refers to any non-aromatic hydrocarbon ring, preferably having five to twelve atoms comprising the ring.

The terms "purified," "substantially purified," and "isolated" as used herein refer to the compound of the invention being free of other, dissimilar compounds with which the compound of the invention is normally associated in its natural state, so that the compound of the invention comprises at least 0.5%, 1%, 5%, 10%, or 20%, and most preferably at least 50% or 75% of the mass, by weight, of a given sample.

The compound of Formula (I) may be obtained and purified as set forth below.

Producing Organisms

One microorganism which may be used for the production of macrocyclic lactams is a strain isolated from a marine sediment sample collected in Bahamas. The culture (strain NPS1583) was deposited on Jan. 21, 2003 with the American Type Culture Collection (ATCC) in Rockville, Md. and assigned the ATCC patent deposition number PTA-4943. The ATCC deposit meets all of the requirements of the Budapest treaty. The culture is also maintained at and available from Nereus Pharmaceutical Culture Collection at 10480 Wateridge Circle, San Diego, Calif. 92121. In addition to the specific microorganism described herein, it should be understood that mutants, such as those produced by the use of chemical or physical mutagens including X-rays, etc. and organisms whose genetic makeup has been modified by molecular biology techniques, may also be cultivated to produce macrocyclic lactam compounds.

Fermentation of Strain NPS1583

The production of macrocyclic lactam compounds may be carried out by cultivating strain NPS1583 in a suitable nutrient medium under conditions described herein, preferably under submerged aerobic conditions, until a substantial amount of compounds are detected in the fermentation; harvesting by extracting the active components from the mycelial growth with a suitable solvent; concentrating the solution containing the desired components; then subjecting the concentrated material to chromatographic separation to isolate the compounds from other metabolites also present in the cultivation medium.

Production of compounds can be achieved at temperature conducive to satisfactory growth of the producing organism, e.g. from 16 degree C. to 40 degree C., but it is preferable to conduct the fermentation at 22 degree C. to 32 degree C. The aqueous medium can be incubated for a period of time necessary to complete the production of compounds as monitored by high pressure liquid chromatography (HPLC), preferably for a period of about 2 to 10 days, on a rotary shaker operating at about 50 rpm to 300 rpm, preferably at 150 rpm to 250 rpm, for example.

Growth of the microorganisms may be achieved by one of ordinary skill of the art by the use of appropriate medium. Broadly, the sources of carbon include glucose, fructose, mannose, maltose, galactose, mannitol and glycerol, other sugars and sugar alcohols, starches and other carbohydrates, or carbohydrate derivatives such as dextran, cerelose, as well as complex nutrients such as oat flour, corn meal, millet, corn, and the like. The exact quantity of the carbon source that is utilized in the medium will depend in part, upon the other ingredients in the medium, but an amount of carbohydrate between 0.5 to 25 percent by weight of the medium can be satisfactorily used, for example. These carbon sources can be used individually or several such carbon sources may be combined in the same medium, for example. Certain carbon sources are preferred as hereinafter set forth.

The sources of nitrogen include amino acids such as glycine, arginine, threonine, methionine and the like, ammonium salt, as well as complex sources such as yeast extracts, corn steep liquors, distiller solubles, soybean meal, cottonseed meal, fish meal, and the like. The various sources of nitrogen can be used alone or in combination in amounts ranging from 0.5 to 25 percent by weight of the medium, for example.

Among the nutrient inorganic salts, which can be incorporated in the culture media, are the customary salts capable of yielding sodium, potassium, magnesium, calcium, phosphate, sulfate, chloride, carbonate, and like ions. Also included are trace metals such as cobalt, manganese, iron, molybdenum, zinc, cadmium, and the like.

The following is one exemplary fermentation protocol that can be utilized for preparing a 20 L batch of organisms that include macrocyclic lactams:

1. Inoculate the starting culture or the freeze culture into 10 ml seed medium and incubate at 28 C and 250 rpm for 3 days.

2. Transfer~4 ml of the above seed culture into 100-ml seed medium in a 500-ml flask (inoculate 2 flasks). Incubate the flasks at 28 C and 250 rpm on a rotary shaker for 3 days.

3. Inoculate 5 ml each of the second seed culture into 20 500-ml flasks containing 100 ml seed medium. Incubate these flasks at 28 C and 250 rpm on a rotary shaker for 3 days.

4. Inoculate 5 ml each of the third seed culture into 200 500-ml flasks containing 100 ml production medium. Incubate these flasks at 28 C and 250 rpm on a rotary shaker for 4 days.

5. Add sterile XAD-16 resin (~3 grams) to each flask. Return the flasks to the shaker and incubate at 28 C and 250 rpm for additional 3 days.

6. Filter the broth to recover the resin and cell mass. Extract the resin-cell mass with 20 liter of methylene chloride/methanol (1:1). The extract is dried in vacuo and submitted to Chemistry for the isolation of macrocyclic lactam.

The pure substance can be isolated from the fermentation product as described below. The present macrocyclic lactams have a unique UV chromophore due to the conjugated macrocyclic lactam ring structure. FIG. 1 depicts an HPLC chromatograph showing the macrocyclic lactam peak and a major, unrelated peak. The macrocyclic lactam can be substantially insoluble.

The pure compound may be obtained by HPLC chromatography as described below:

Column: ACE 5 C18-HL
Dimensions: 15 cm×21 mm ID
Flow rate: 14.5 ml/min
Detection: 290 nm
Solvent: $H_2O$/Acetonitrile gradient (100% H2O TO 20% $H_2O$/ACN) in 14 minutes.

50 mg of the crude extract is dissolved in methanol/DMSO (80% MeOH/20% DMSO, 900 µl) and this solution is injected on the HPLC column. The desired compound elutes with a retention time of 12 minutes using the solvent gradient described above.

Alternatively, an improved method of isolation involves the precipitation of the compound directly from a solution of the crude extract. In this method, a concentrated DMSO solution of the crude microbial extract (50–250 mg, 100 mg/ml) is slowly added to a solution of methylene chloride and $H_2O$ (100 ml each). After complete addition of the crude extract and agitation of the solution, a white precipitate forms in the $H_2O$ solvent layer. Following separation of the $H_2O$ and methylene chloride layers, the precipitated compound can be obtained by centrifugation of the aqueous solution. The final purification involves repeated trituration of the precipitate using cold methanol solutions to dissolve remaining impurities to yield 20 mg pure material.

For larger scale preparation of the compound, a method which involves trituration of the dried crude extract with hexanes to remove large amounts of contaminants is preferred. Further purification of the remaining enriched precipitate by preparative C18 HPLC, eluting with an isocratic 75% methanol/25% water isocratic gradient, provides compound with purities measured at greater than 90%.

The compound has the following characteristics as elucidated by the methods described below: Formula, $C_{28}H_{39}NO_4$; Exact Mass: 453.2962; Mol. Wt. 453.61; C-74.14; H-8.67; N-3.09; O-14.11.

Figure 2:
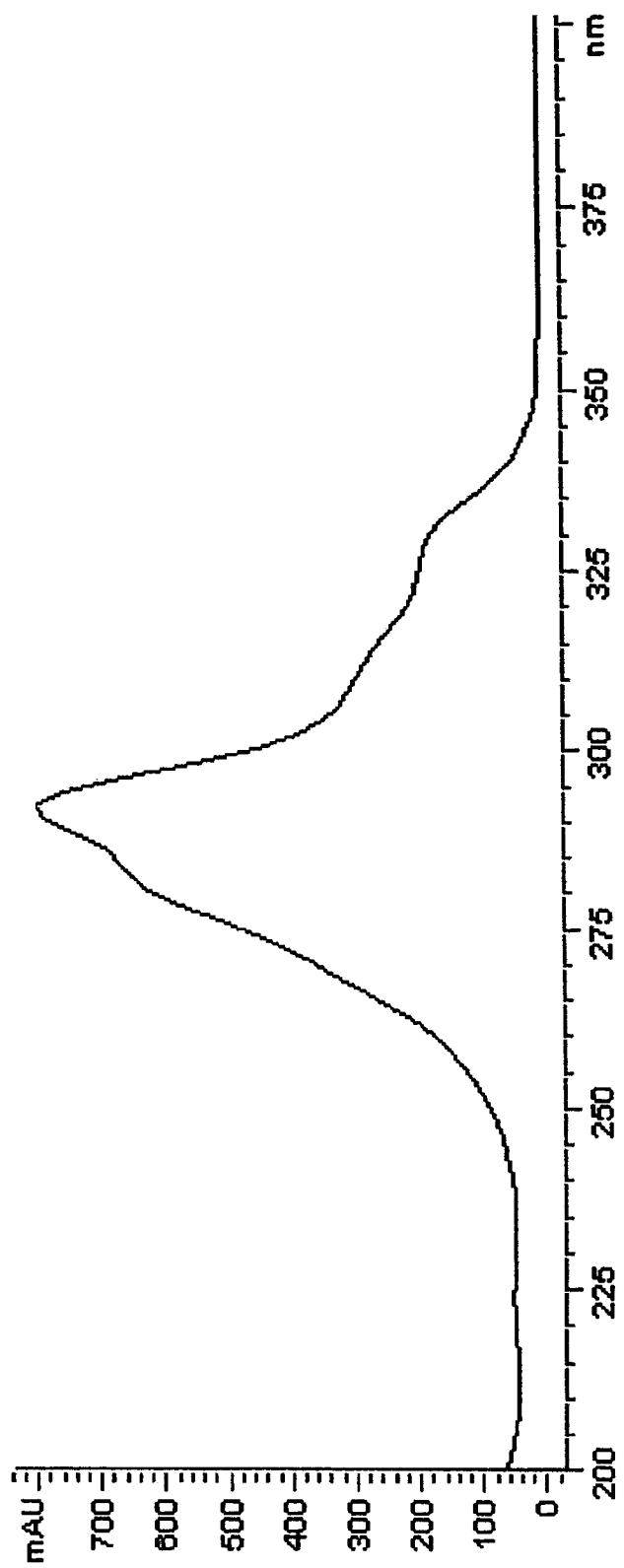
FIG. 2 depicts the UV spectrum of a compound of the invention in acetonitrile/$H_2O$.
Figure 3:
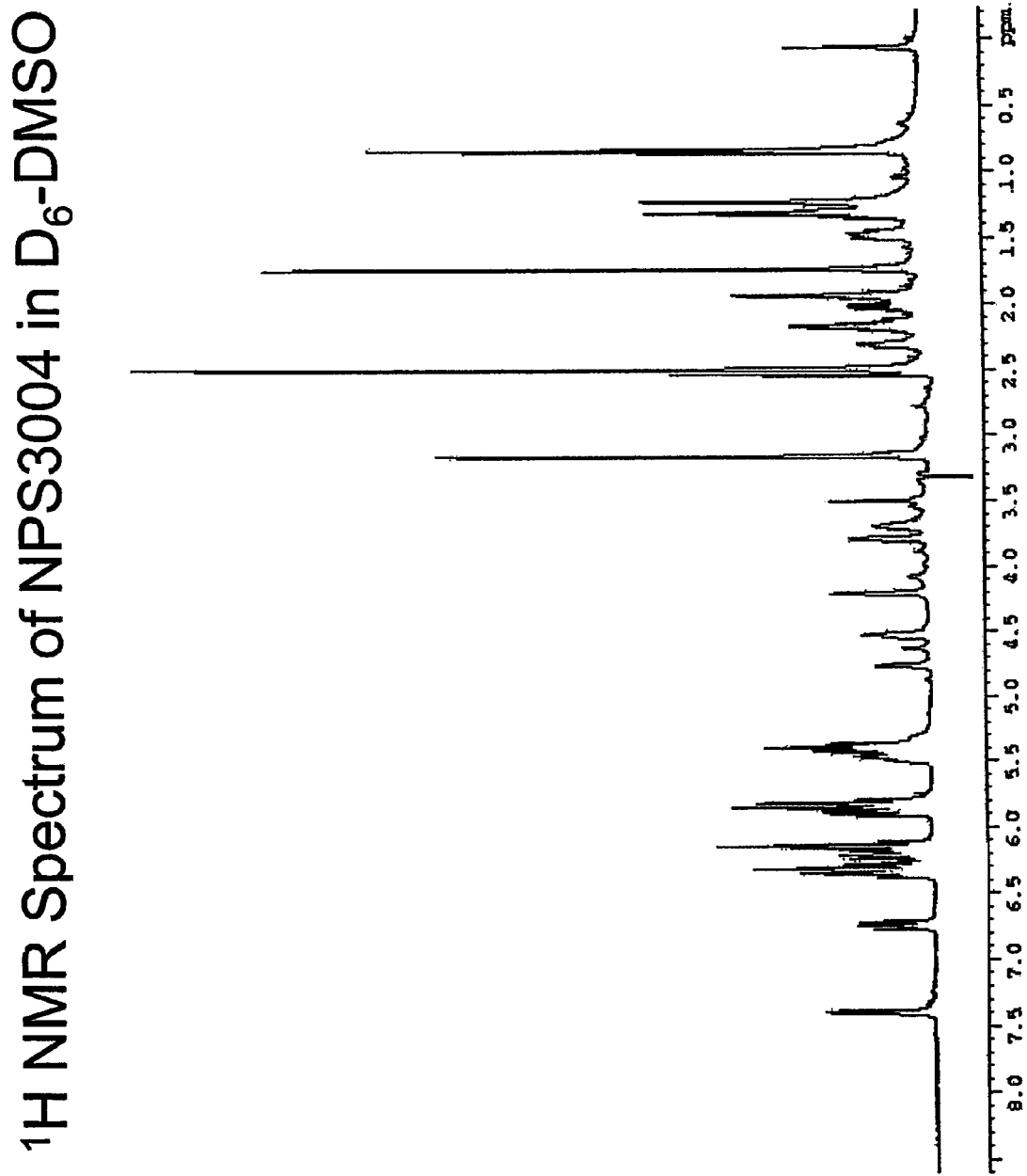
FIG. 3 depicts the $^1H$ NMR spectrum of a compound of the invention in $D_6$-DMSO.
Figure 4:
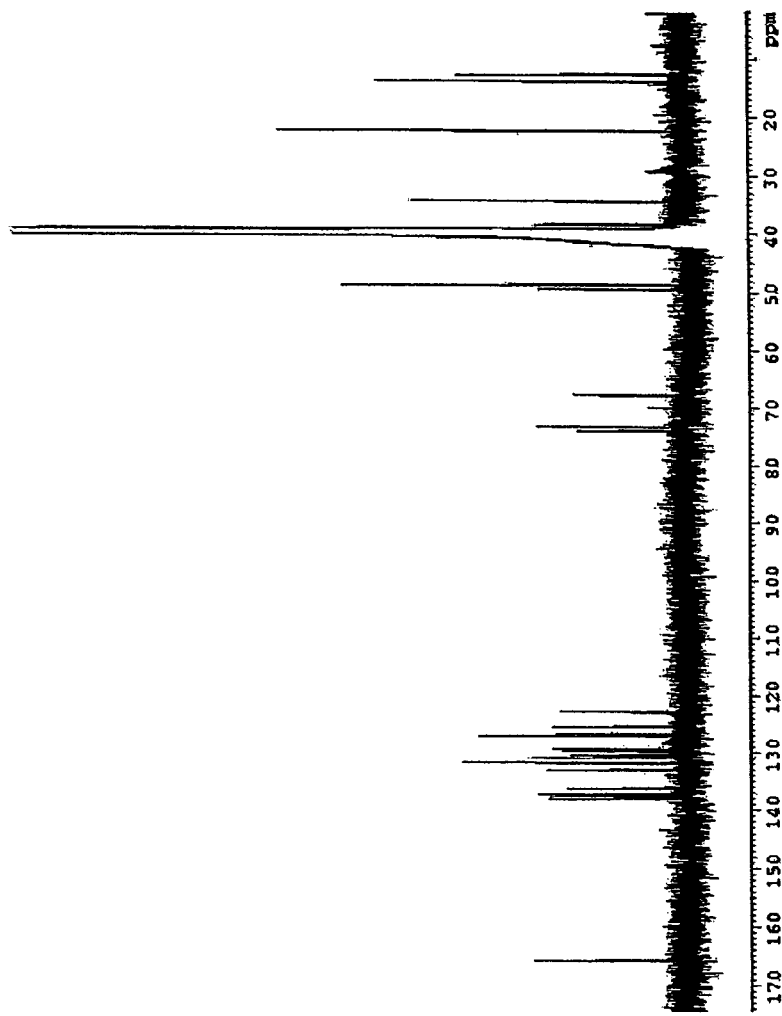
FIG. 4 depicts the $^{13}C$ NMR spectrum of a compound of the invention in $D_6$-DMSO.

The structure of the purified compound can be elucidated by various methods, including NMR, MS, and UV. FIGS. 2–4 provide spectral data from these methods. FIG. 2 depicts the UV spectrum of the compound in acetonitrile/$H_2O$. FIG. 3 depicts the $^1H$ NMR spectrum of the compound in $D_6$-DMSO. FIG. 4 depicts the $^{13}C$ NMR spectrum of the compound in $D_6$-DMSO.

Furthermore, using UV spectrometry and mass spectrometry structural assignments can be elucidated for the compound with the structure of Formula (I):

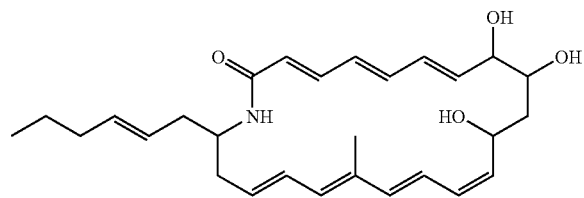

UV spectrometry: $\lambda_{max}$=290 nm, shoulder 283, 310, 330 nm.

Mass spectrometry: HR ESI-TOF: M+H m/z=454.2962, $\Delta_{calc}$ $C_{28}H_{40}NO_4$=1.1 ppm

TABLE 1

| NMR Assignments for 1583-05-AB-453 | | |
|---|---|---|
| POSITION | $^{13}C^*$ | $^1H$, int, mult, J (Hz) |
| NH | | 7.30, 1H, bd |
| 1 | 165.9 | |
| 2 | 125.54 | 5.83, 1H, d, 16.0 |
| 3 | 138.01 | 6.74, 1H, dd, 15.1, 10.6 |
| 4 | 129.79 | 6.21, 1H, m |
| 5 | 137.44 | 6.33, 1H, m |
| 6 | 129.38 | 6.27, 1H, m |
| 7 | 137.68 | 5.80, 1H, dd, 14.5, 5.3 |
| 8 | 73.1 | 4.23, 1H, br m |
| 9 | 73.82 | 3.80, 1H, m |
| 10 | 38.2 | 1.46 |
| | | 1.29 |
| 11 | 67.58 | 4.54, 1H, m |
| 12 | 136.3 | 5.39, 1H, m |
| 13 | 126.79 | 5.85, 1H, m |
| 14 | 122.82 | 6.15, 1H, m |
| 15 | 137.27 | 6.12, 1H, d, 15.4 |
| 16 | 133.11 | |
| 17 | 130.83 | 5.89, 1H, d, 12.3 |
| 18 | 130.95 | 6.35, 1H, m |
| 19 | 130.47 | 5.49, 1H, m |
| 20 | 38.14 | 2.32, 1H, m |
| | | 2.05, 1H, m |
| 21 | 49.29 | 3.71, 1H, m |
| 22 | 38.29 | 2.19, 2H, m |
| 23 | 127.16 | 5.39, 1H, m |
| 24 | 131.8 | 5.42, 1H, m |
| 25 | 34.11 | 1.95, 2H, m |
| 26 | 22.06 | 1.31, 2H, m |
| 27 | 13.42 | 0.85, 3H, t, 7.2 |
| 28 | 12.35 | 1.74, 3H, s |
| OH (C8) | | 4.67 1H, br m |
| OH (C9) | | 4.62, 1H, br m |
| OH (C11) | | 4.51, 1H, br m |

TABLE 1-continued

| NMR Assignments for 1583-05-AB-453 | | |
|---|---|---|
| POSITION | $^{13}C^*$ | $^1H$, int, mult, J (Hz) |

*All NMR data reported in $D_6$-DMSO referenced to residual solvent signals at 2.49 ($^1H$) or 39.5 ppm ($^{13}C$).

The compound is novel with no obvious relation to other chemistry. The present compound contains multiple (4) stereocenters; however the NMR data indicate that these molecules are in a fixed conformation and are very pure.

The compound exhibits both antimicrobial and anti-tumor activity. The compound was screened in 7 antimicrobial screens with the results shown below in Tables 3–4 shown in Example 5.

Figure 5:
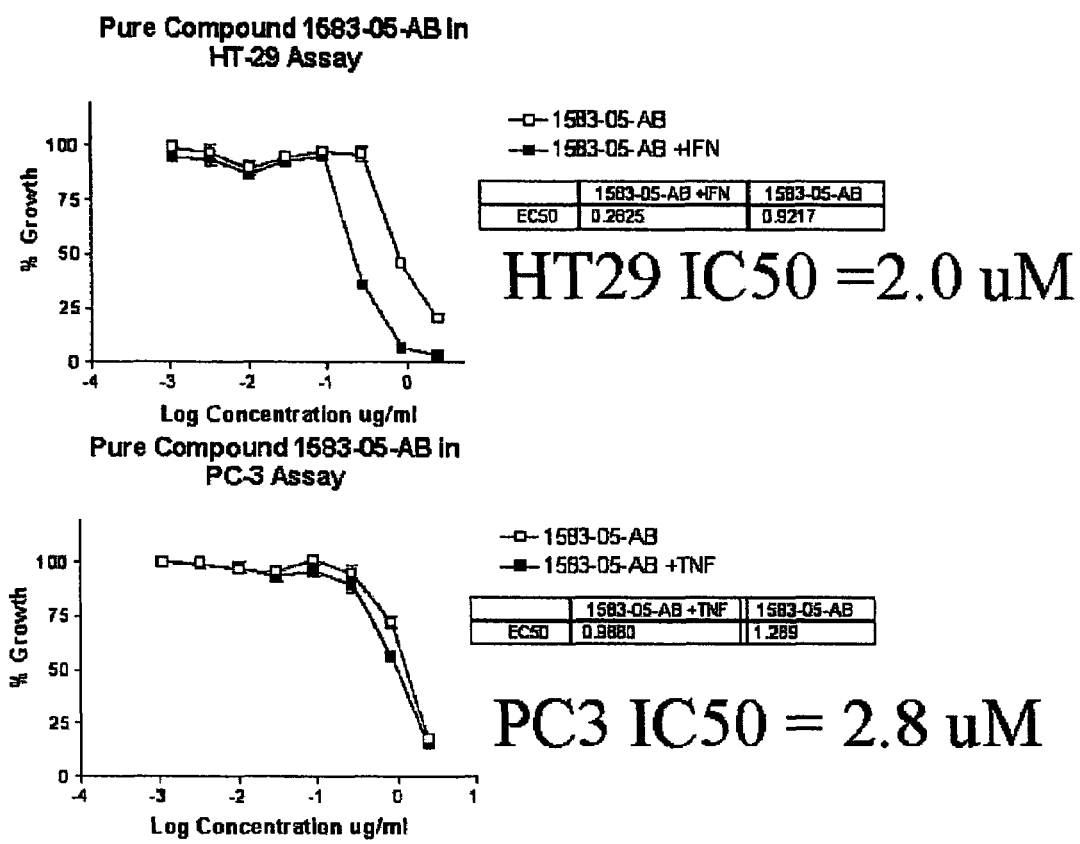
FIG. 5 depicts the results of assays showing the anti-tumor activity for a compound of the invention.

FIG. 5 depicts the results of assays showing the anti-tumor activity for the compound. The pure compound was tested in an HT-29 assay and in a PC3 assay with the results set forth in FIG. 5. EC50 values in the HT-29 assay were 0.2625 µg/ml (0.58 µM) for the compound with interferon and 0.9217 µg/ml (2.03 µM) for the compound alone. The EC50 values for the PC3 assay were 0.9880 µg/ml (2.18 µM) for the compound with TNF-α (alpha) and 1.289 µg/ml (2.84 µM) for the compound alone. Thus, the compound is very active with indications of selectivity.

Also the compound of Formula (I) was tested against and showed activity against Jurkat human T cell leukemia cells and B16-F10 mouse melanoma cells. The EC50 values from one set of evaluations for the Jurkat cells were 2.33±1.11 and for the B16-F10 cells were 2.16±0.87.

The compound exhibits good drugability. It obeys the chemists' "Lipinski Rule of 5" for determining drug-like characteristics in a molecule (related to absorption and permeability). There are fewer than 5H-bond donors (sum of OHs and NHs). The compound has 4. There are fewer than 10H-bond acceptors (expressed as the sum of Ns and Os). As set forth below, consistent therewith, the compound can be used as pharmaceutical compounds and in pharmaceutical compositions.

Pharmaceutical Compositions

Embodiments of the present invention also relate to the compounds disclosed herein used in pharmaceutical compositions. The compounds can optionally and preferably produced by the methods disclosed herein. The compounds can be used, for example, in pharmaceutical compositions comprising a pharmaceutically acceptable carrier prepared for storage and subsequent administration. Also, embodiments relate to a pharmaceutically effective amount of the products and compounds disclosed above in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985), which is incorporated herein by reference in its entirety. Preservatives, stabilizers, dyes and even flavoring agents may be provided in the pharmaceutical composition. For example, sodium benzoate, ascorbic acid and esters of p-hydroxybenzoic acid may be added as preservatives. In addition, antioxidants and suspending agents may be used.

The macrocyclic lactam and analog compositions may be formulated and used as tablets, capsules, or elixirs for oral administration; suppositories for rectal administration; sterile solutions, suspensions for injectable administration; patches for transdermal administration, and sub-dermal deposits and the like. Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or other organic oils such as soybean, grapefruit or almond oils, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. Such formulations can be made using methods known in the art. See, for example, U.S. Pat. No. 5,733,888 (injectable compositions); U.S. Pat. No. 5,726,181 (poorly water soluble compounds); U.S. Pat. No. 5,707,641 (therapeutically active proteins or peptides); U.S. Pat. No. 5,667,809 (lipophilic agents); U.S. Pat. No. 5,576,012 (solubilizing polymeric agents); U.S. Pat. No. 5,707,615 (anti-viral formulations); U.S. Pat. No. 5,683,676 (particulate medicaments); U.S. Pat. No. 5,654,286 (topical formulations); U.S. Pat. No. 5,688,529 (oral suspensions); U.S. Pat. No. 5,445,829 (extended release formulations); U.S. Pat. No. 5,653,987 (liquid formulations); U.S. Pat. No. 5,641,515 (controlled release formulations) and U.S. Pat. No. 5,601,845 (spheroid formulations); all of which are incorporated herein by reference in their entireties.

Further disclosed herein are various pharmaceutical compositions well known in the pharmaceutical art for uses that include intraocular, intranasal, and intraauricular delivery. Pharmaceutical formulations include aqueous ophthalmic solutions of the active compounds in water-soluble form, such as eyedrops, or in gellan gum (Shedden et al., *Clin. Ther.*, 23(3):440–50 (2001)) or hydrogels (Mayer et al., *Ophthalmologica*, 210(2):101–3 (1996)); ophthalmic ointments; ophthalmic suspensions, such as microparticulates, drug-containing small polymeric particles that are suspended in a liquid carrier medium (Joshi, A., *J. Ocul. Pharmacol.*, 10(1):29–45 (1994)), lipid-soluble formulations (Alm et al., *Prog. Clin. Biol. Res.*, 312:447–58 (1989)), and microspheres (Mordenti, *Toxicol. Sci.*, 52(1):101–6 (1999)); and ocular inserts. All of the above-mentioned references, are incorporated herein by reference in their entireties. Such suitable pharmaceutical formulations are most often and preferably formulated to be sterile, isotonic and buffered for stability and comfort. Pharmaceutical compositions may also include drops and sprays often prepared to simulate in many respects nasal secretions to ensure maintenance of normal ciliary action. As disclosed in Remington's Pharmaceutical Sciences (Mack Publishing, 18$^{th}$ Edition), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

When used as an anti-cancer or anti-microbial/infectious disease compound, the compound of Formula (I) or compositions including Formula (I) can be administered by either oral or a non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intreperitoneally, intravenously, intramuscularly, or the like. Similarly, it may be administered topically, rectally, or vaginally, as deemed appropriate by those of skill in the art for bringing the compound of the invention into optimal contact with a tumor, thus inhibiting the growth of the tumor. Local administration at the site of the cancer/tumor is also contemplated, either before or after tumor resection, as are controlled release formulations, depot formulations, and infusion pump delivery.

Methods of Administration

The present invention also encompasses methods for making and for administering the disclosed chemical compounds and the disclosed pharmaceutical compositions. Such disclosed methods include, among others, (a) administration though oral pathways, which administration includes administration in capsule, tablet, granule, spray, syrup, or other such forms; (b) administration through non-oral pathways, which administration includes administration as an aqueous suspension, an oily preparation or the like or as a drip, suppository, salve, ointment or the like; administration via injection, subcutaneously, intraperitoneally, intravenously, intramuscularly, intradermally, or the like; as well as (c) administration topically, (d) administration rectally, or (e) administration vaginally, as deemed appropriate by those of skill in the art for bringing the compound of the invention into contact with living tissue; and (f) administration via controlled released formulations, depot formulations, and infusion pump delivery. As further examples of such modes of administration and as further disclosure of modes of administration, disclosed herein are various methods for administration of the disclosed chemical compounds and pharmaceutical compositions including modes of administration through intraocular, intranasal, and intraauricular pathways.

The pharmaceutically effective amount of the macrocyclic lactam and analog composition required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In practicing the methods of the invention, the products or compositions can be used alone or in combination with one another, or in combination with other therapeutic or diagnostic agents. These products can be utilized in vivo, ordinarily in a mammal, preferably in a human, or in vitro. In employing them in vivo, the products or compositions can be administered to the mammal in a variety of ways, including parenterally, intravenously, subcutaneously, intramuscularly, colonically, rectally, vaginally, nasally or intraperitoneally, employing a variety of dosage forms. Such methods may also be applied to testing chemical activity in vivo.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved or adverse side effects disappear. The dosage may range broadly, depending upon the desired affects and the therapeutic indication. Typically, dosages may be between about 10 microgram/kg and 100 mg/kg body weight, preferably between about 100 microgram/kg and 10 mg/kg body weight. Alternatively dosages may be based and calculated upon the surface area of the patient, as understood by those of skill in the art. Administration is preferably oral on a daily or twice daily basis.

The exact formulation, route of administration and dosage can be chosen by the individual physician in view of the patient's condition. See for example, Fingl et al., in The Pharmacological Basis of Therapeutics, 1975, which is incorporated herein by reference in its entirety. It should be noted that the attending physician would know how to and when to terminate, interrupt, or adjust administration due to toxicity, or to organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency, will also vary according to the age, body weight, and response of the individual patient. A program comparable to that discussed above may be used in veterinary medicine.

Depending on the specific conditions being treated, such agents may be formulated and administered systemically or locally. A variety of techniques for formulation and administration may be found in Remington's Pharmaceutical Sciences, 18th Ed., Mack Publishing Co., Easton, Pa. (1990), which is incorporated herein by reference in its entirety. Suitable administration routes may include oral, rectal, transdermal, vaginal, transmucosal, or intestinal administration; parenteral delivery, including intramuscular, subcutaneous, intramedullary injections, as well as intrathecal, direct intraventricular, intravenous, intraperitoneal, intranasal, or intraocular injections.

For injection, the agents of the invention may be formulated in aqueous solutions, preferably in physiologically compatible buffers such as Hanks' solution, Ringer's solution, or physiological saline buffer. For such transmucosal administration, penetrants appropriate to the barrier to be permeated are used in the formulation. Such penetrants are generally known in the art. Use of pharmaceutically acceptable carriers to formulate the compounds herein disclosed for the practice of the invention into dosages suitable for systemic administration is within the scope of the invention. With proper choice of carrier and suitable manufacturing practice, the compositions disclosed herein, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a patient to be treated.

Agents intended to be administered intracellularly may be administered using techniques well known to those of ordinary skill in the art. For example, such agents may be encapsulated into liposomes, then administered as described above. All molecules present in an aqueous solution at the time of liposome formation are incorporated into the aqueous interior. The liposomal contents are both protected from the external micro-environment and, because liposomes fuse with cell membranes, are efficiently delivered into the cell cytoplasm. Additionally, due to their hydrophobicity, small organic molecules may be directly administered intracellularly.

Determination of the effective amounts is well within the capability of those skilled in the art, especially in light of the detailed disclosure provided herein. In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The pharmaceutical compositions may be manufactured in a manner that is itself known, for example, by means of conventional mixing, dissolving, granulating, dragee-making, levitating, emulsifying, encapsulating, entrapping, or lyophilizing processes.

Compounds disclosed herein can be evaluated for efficacy and toxicity using known methods. For example, the toxicology of a particular compound, or of a subset of the compounds, sharing certain chemical moieties, may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several art recognized methods, such as in vitro methods, animal models, or human clinical trials. Art-recognized in vitro models exist for nearly every class of condition, including the conditions abated by the compounds disclosed herein, including cancer, cardiovascular disease, and various immune dysfunction. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

When used as an anti-cancer agent, a tumor-growth-inhibiting compound, or antimicrobial, the compounds disclosed herein may be administered by either oral or a non-oral pathways. When administered orally, it can be administered in capsule, tablet, granule, spray, syrup, or other such form. When administered non-orally, it can be administered as an aqueous suspension, an oily preparation or the like or as a drip, suppository, salve, ointment or the like, when administered via injection, subcutaneously, intraperitoneally, intravenously, intramuscularly, intradermally, or the like. Similarly, it may be administered topically, rectally, or vaginally, as deemed appropriate by those of skill in the art for bringing the compound of the invention into optimal contact with a tumor, thus inhibiting the growth of the tumor. Local administration at the site of the tumor or other disease condition is also contemplated, either before or after tumor resection, or as part of an art-recognized treatment of the disease condition. Controlled release formulations, depot formulations, and infusion pump delivery are similarly contemplated.

When used as an anti-cancer agent, an anti-tumor agent, or as an antimicrobial, the compound may be orally or non-orally administered to a human patient in the amount of about 0.0007 mg/day to about 7,000 mg/day of the active ingredient, and more preferably about 0.07 mg/day to about 70 mg/day of the active ingredient at, preferably, one time per day or, less preferably, over two to about ten times per day. Alternatively and also preferably, the compound of the invention may preferably be administered in the stated amounts continuously by, for example, an intravenous drip. Thus, for a patient weighing 70 kilograms, the preferred daily dose of the active anti-tumor ingredient would be about 0.0007 mg/kg/day to about 35 mg/kg/day, and more preferable, 0.007 mg/kg/day to about 0.035 mg/kg/day. Nonetheless, as will be understood by those of skill in the art, in certain situations it may be necessary to administer the anti-tumor compound of the invention in amounts that excess, or even far exceed, the above-stated, preferred dosage range to effectively and aggressively treat particularly advanced or lethal tumors.

To formulate the dosage including the compounds disclosed herein as a tumor-growth-inhibiting compound or antimicrobials, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents. In addition to the foregoing preferred ingredients, sweeteners, fragrances, colorants, preservatives and the like may be added to the administered formulation of the compound of the invention, particularly when the compound is to be administered orally.

The compositions disclosed herein in pharmaceutical compositions may also comprise a pharmaceutically acceptable carrier. Such compositions may be prepared for storage and for subsequent administration. Acceptable carriers or diluents for therapeutic use are well known in the pharmaceutical art, and are described, for example, in Remington's Pharmaceutical Sciences, Mack Publishing Co. (A. R. Gennaro edit. 1985). For example, such compositions may be formulated and used as tablets, capsules or solutions for oral administration; suppositories for rectal or vaginal administration; sterile solutions or suspensions for injectable administration. Injectables can be prepared in conventional forms, either as liquid solutions or suspensions, solid forms suitable for solution or suspension in liquid prior to injection, or as emulsions. Suitable excipients include, but are not limited to, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. If desired, absorption enhancing preparations (for example, liposomes), may be utilized.

The pharmaceutically effective amount of the composition required as a dose will depend on the route of administration, the type of animal being treated, and the physical characteristics of the specific animal under consideration. The dose can be tailored to achieve a desired effect, but will depend on such factors as weight, diet, concurrent medication and other factors which those skilled in the medical arts will recognize.

The products or compositions of the invention, as described above, may be used alone or in combination with one another, or in combination with other therapeutic or diagnostic agents. These products can be utilized in vivo or in vitro. The useful dosages and the most useful modes of administration will vary depending upon the age, weight and animal treated, the particular compounds employed, and the specific use for which these composition or compositions are employed. The magnitude of a dose in the management or treatment for a particular disorder will vary with the severity of the condition to be treated and to the route of administration, and depending on the disease conditions and their severity, the compositions may be formulated and administered either systemically or locally. A variety of techniques for formulation and administration may be found in Remington's Pharmaceutical Sciences, 18th ed., Mack Publishing Co., Easton, Pa. (1990).

To formulate the compounds of Formula (I) as a tumor-growth-inhibiting, anticancer compound, or antimicrobial, known surface active agents, excipients, smoothing agents, suspension agents and pharmaceutically acceptable film-forming substances and coating assistants, and the like may be used. Preferably alcohols, esters, sulfated aliphatic alcohols, and the like may be used as surface active agents; sucrose, glucose, lactose, starch, crystallized cellulose, mannitol, light anhydrous silicate, magnesium aluminate, magnesium methasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents. In addition to the foregoing preferred ingredients, sweeteners, fragrances, colorants, preservatives and the like may be added to the administered formulation of the compound produced by the method of the invention, particularly when the compound is to be administered orally.

The compounds and compositions may be orally or non-orally administered to a human patient in the amount of about 0.001 mg/kg/day to about 10,000 mg/kg/day of the active ingredient, and more preferably about 0.1 mg/kg/day to about 100 mg/kg/day of the active ingredient at, preferably, one time per day or, less preferably, over two to about ten times per day. Alternatively and also preferably, the compound produced by the method of the invention may preferably be administered in the stated amounts continuously by, for example, an intravenous drip. Thus, for the example of a patient weighing 70 kilograms, the preferred daily dose of the active anti-tumor ingredient would be about 0.07 mg/day to about 700 gm/day, and more preferable, 7 mg/day to about 7 grams/day. Nonetheless, as will be understood by those of skill in the art, in certain situations it may be necessary to administer the anti-tumor compound produced by the method of the invention in amounts that excess, or even far exceed, the above-stated, preferred dosage range to effectively and aggressively treat particularly advanced or lethal tumors.

In the case of using the anti-tumor, anticancer or antimicrobial produced by methods of the invention as a biochemical test reagent, the compound produced by methods of the invention inhibits the progression of the disease when it is dissolved in an organic solvent or hydrous organic solvent and it is directly applied to any of various cultured cell systems. Usable organic solvents include, for example, methanol, methylsulfoxide, and the like. The formulation can, for example, be a powder, granular or other solid inhibitor, or a liquid inhibitor prepared using an organic solvent or a hydrous organic solvent. While a preferred concentration of the compound produced by the method of the invention for use as an antimicrobial, anticancer or anti-tumor compound is generally in the range of about 1 to about 100 μg/ml, the most appropriate use amount varies depending on the type of cultured cell system and the purpose of use, as will be appreciated by persons of ordinary skill in the art. Also, in certain applications it may be necessary or preferred to persons of ordinary skill in the art to use an amount outside the foregoing range.

The following non-limiting examples are meant to describe the preferred methods of the invention using certain preferred embodiments of the invention. Variations in the details of the particular methods employed and in the precise chemical compositions obtained will undoubtedly be appreciated by those of skill in the art.

EXAMPLE 1

Fermentation Protocol

Strain NPS1583 was grown in a 40 ml tube containing 10 ml of vegetative medium consisting of the following per liter of sea water: starch, 10 g; yeast extract, 4 g; and peptone, 2 g. The culture was allowed to incubate for 3 days at 28 degree C. on a rotary shaker operating at 250 rpm. The vegetative culture was mixed with 2 ml of cryoprotective solution consisting of 500 g glycerol per liter of deionized water. 1.5 ml portions of this mixture were transferred to sterile cryogenic tube (2 ml capacity). The vegetative cultures so obtained were frozen and stored at −80 degree C.

Seed culture for the production of NPS1583 compounds was prepared by transferring 1.5 ml of the cryopreservative culture to a 40 ml tube containing 10 ml of sterile vegetative medium having the same composition as the above. The seed culture was incubated at 28 degree C. for 3 days on a rotary shaker operating at 250 rpm. Four ml of this seed culture was inoculated into 500 ml flask containing 100 ml of the vegetative medium (two flasks inoculated). The second seed cultures were incubated at 28 degree C. for 3 days on a rotary shaker operating at 250 rpm. Five ml each of the second seed culture was inoculated into twenty 500 ml flask containing 100 ml of the vegetative medium. The third seed cultures were incubated at 28 degree C. for 3 days on a rotary shaker operating at 250 rpm. Five ml each of the third seed culture was inoculated into the production medium consisting of the following per liter of sea water: starch, 5 g; Hydro Solubles, 4 ml; Menhaden fish meal, 2 g; Kelp powder, 2 g; and chitosan, 2 g. The production culture was incubated at 28 degree C. for 4 days on a rotary shaker operating at 250 rpm. Sterile XAD-16 resin (~3 grams) was added to each flask. The flasks were returned to the shaker and incubated at 28 degree C. and 250 rpm for additional 3 days. The culture broth was filter through cheese cloth to recover the cell mass and XAD-16 resin. The cell mass-resin was extracted with 20 liters of methylene chloride/methanol (1:1). The extract was dried in vacuo. The dried extract, containing the NPS1583 compounds, was then processed for the recovery of NPS1583 compounds.

The pure substance was isolated from the fermentation product as described in Example 2. The macrocyclic lactams had a unique UV chromophore due to the conjugated macrocyclic lactam ring structure. FIG. 1 shows an HPLC chromatograph showing the macrocyclic lactam peak and other metabolite peaks. The macrocyclic lactam can be substantially insoluble.

EXAMPLE 2

Purification of the Compound

The pure compound was obtained by HPLC chromatography as described below:
Column: ACE 5 C18-HL
Dimensions: 15 cm×21 mm ID
Flow rate: 14.5 ml/min
Detection: 290 nm
Solvent: $H_2O$/Acetonitrile gradient (100% $H_2O$ TO 20% $H_2O$/ACN) in 14 minutes.

50 mg of the crude extract was dissolved in methanol/DMSO (80% MeOH/20% DMSO, 900 µl) and this solution is injected on the HPLC column. The desired compound eluted with a retention time of 12 minutes using the solvent gradient described above.

Alternatively, an improved method of isolation involved the precipitation of the compound directly from a solution of the crude extract. In this method, a concentrated DMSO solution of the crude microbial extract (100 mg/ml) was slowly added to a solution of methylene chloride and $H_2O$ (100 ml each). After complete addition of the crude extract and agitation of the solution, a white precipitate formed in the $H_2O$ solvent layer. Following separation of the $H_2O$ and methylene chloride layers, the precipitated compound was obtained by centrifugation of the aqueous solution. The final purification involved repeated trituration of the precipitate using cold methanol solutions to dissolve remaining impurities to yield 20 mg pure material.

EXAMPLE 3

Semisynthesis of Macrocyclic Lactams

Semi-Synthesis of Triacetate Macrocyclic Lactam:

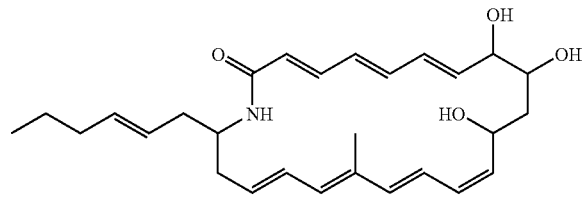

5.2 mg of the tri-hydroxy macrocyclic lactam compound shown above was mixed with anhydrous pyridine (0.1 ml) and combined with acetic anhydride (1.5 ml), and the resulting solution stirred at room temperature for 48 hours or until the starting material was completely in solution. The reaction was quenched by addition of ice and extraction with methylene chloride. The organic extract was purified by HPLC chromatography to yield 1.6 mg of the triacetate derivative of the tri-hydroxy macrocyclic lactam.

The following compound was isolated:

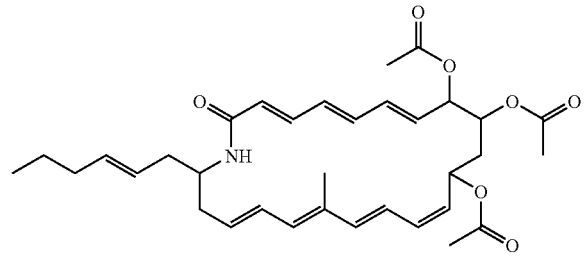

The following data were gathered for the compound: $^1$H NMR (500 MHz, DMSO-$D_6$) 7.44 (1H, d, 9.6 Hz) NH; 6.74 (1H, m) H3; 6.40–6.22 (5H, overlapped multiplets); 6.02 (1H, dd, 11.8 11.8); 5.95 (1H, d, 11.2 Hz); 5.89 (1H, m); 5.88 (1H, d, 15.3 Hz) H2; 5.72 (1H, m) H9; 5.53–5.37 (5H, overlapped multiplets); 5.32 (1H, dd, 9.6, 7.8 Hz) H8; 5.21 (1H, m) H11; 3.75 (1H, m) H21; 2.35 (1H, m) H20a; 2.17 (2H, m, H22); 2.06 (3H, s) acetate methyl; 2.06 (1H, m) H20b; 1.99 (3H, s) acetate methyl; 1.98 (3H, s) acetate methyl; 1.97 (2H, m) H25; 1.95 (1H, m) H10a; 1.81 (3H, s) H28; 1.73 (1H, m) H10b; 1.33 (2H, m) H26; 0.848 (3H, t) H27.

ESI-HRMS: M+H 580.3269 (calc. $C_{34}H_{46}NO_7$=580.3274) $\Delta_{calc}$=0.9 ppm, UV: $\lambda_{max}$ 220 nm, 290 nm, 285 nm (sh), 310 nm (sh), 330 nm (sh).

EXAMPLE 4

Biological Characteristics of the Macrocyclic Lactams

A. Biological Evaluation

The biological characteristics of compound of Formula (I) was evaluated in both HT29 human colon cells, PC-3 prostatic adenocarcinoma cells, Jurkat human T cell leukemia, and B16-F10 mouse melanoma cells.

HT-29 (ATCC HTB-38) a human colorectal adenocarcinoma was maintained in McCoy's complete medium (McCoy's 5A medium with L-glutamine and 25 mM HEPES supplemented with 10% FBS, 1 mM Na pyruvate, 1X NEAA, 2 mM L-glutamine, and Pen/Strep at 100 IU/ml and 100 µg/ml, respectively). Cell lines were cultured at 37° C., 5% $CO_2$ in a 95% humidified incubator.

PC-3 (ATCC CRL-1435), a human prostate adenocarcinoma, was maintained in F12K complete medium (F12K medium supplemented with 10% FBS; 2 mM Glutamine; 10 mM HEPES; and Pen/Strep at 100 IU/ml and 100 µg/ml, respectively). Cell lines were cultured at 37° C., 5% $CO_2$ in a 95% humidified incubator.

Jurkat (ATCC TIB-152) a human acute T cell leukemia was maintained in RPMI complete medium (RPMI 1640 medium supplemented with 10% FBS, 2 mM L-glutamine, 10 mM HEPES, 1 mM Na pyruvate, 1X NEAA, and Pen/Strep at 100 IU/ml and 100 µg/ml, respectively). Cell lines were cultured at 37° C., 5% $CO_2$ in a 95% humidified incubator.

B16-F10 (ATCC CRL-6475) a mouse melanoma was maintained in complete DMEM (DMEM supplemented with 10% FBS, 2 mM L-glutamine, 10 mM HEPES, and Pen/Strep at 100 IU/ml and 100 µg/ml, respectively). Cell lines were cultured at 37° C., 5% $CO_2$ in a 95% humidified incubator.

For tumor cytotoxicity assays HT-29, PC-3, or B16-F10 cells were seeded at $5\times10^3$, $5\times10^3$ or $1.25\times10^3$ cells/well cells were seeded at 5,000 cells/well in 90 µl complete media into a Corning 3904 black-walled, clear-bottom tissue culture plate and the plate were incubated overnight to allow cells to establish and enter log phase growth. Jurkat cells were seeded on the day of compound addition at $2\times10^4$ cells/well in 90 µl complete media into a Corning 3904 black-walled, clear-bottom tissue culture plate. 20 mM stock solutions of the compound of Formula (I) were prepared in 100% DMSO and stored at −20° C. 10×concentrated serial dilutions of the compounds were prepared in appropriate culture medium for final concentrations ranging from 2×10–5 to 2×10–12. Ten µl volumes of the 10×serial dilutions were added to the test wells in triplicate and the plates returned to the incubator for 48 hours. The final concentration of DMSO was 0.25% in all samples.

Following 48 hours of drug exposure 10 µl of 0.2 mg/ml resazurin (obtained from Sigma-Aldrich Chemical Co.) in $Mg^{2+}$, $Ca^{2+}$ free PBS was added to each well and the plates were returned to the incubator for 3–4 hours. Because living cells metabolize Resazurin, the fluorescence of the reduction product of Resazurin was measured using a Fusion microplate fluorometer (Packard Bioscience) with $\lambda_{ex}$=535 nm and $\lambda_{em}$=590 nm filters. The plates were removed and resazurin fluorescence was measured using 530 nm excitation and 590 nm emission filters in a Fusion fluorimeter (Packard Instruments). Resazurin dye without cells was used to determine the background, which was subtracted from the data for all experimental wells. The data were analyzed using Prism software (GraphPad Software). The data were normalized to the average of the cells treated with media only (100% cell growth) and $EC_{50}$ values were determined using a standard sigmoidal dose response curve fitting algorithm.

The results were as follows:

FIG. 5 illustrates anti-tumor activity for the compound. The pure compound was tested in an HT-29 assay and in a PC3 assay with the results set forth in FIG. 5. EC50 values in the HT-29 assay were 0.2625 µg/ml (0.58 µM) for the compound with interferon and 0.9217 µg/ml (2.03 µM) for the compound alone. The EC50 values for the PC3 assay were 0.9880 µg/ml (2.18 µM) for the compound with TNF-α (alpha) and 1.289 µg/ml (2.84 µM) for the compound alone. Thus, the compound is very active with indications of selectivity.

Further evaluation of the compound against HT29, B16-F10, and Jurkat cell lines resulted in the EC50 values presented below. Thus, targets for the 22 membered macrocyclic lactams include colon, melanoma, leukemia, and prostate cancers.

TABLE 2

| HT-29 EC50 (µM) | B16-F10 EC50 (µM) | Jurkat EC50 (µM) |
|---|---|---|
| 3.62 ± 2.57 | 2.16 ± 0.87 | 2.33 ± 1.11 |

EXAMPLE 5

Biological Evaluation (Antimicrobial Activity)

The biological characteristics of compound of Formula (I) were evaluated in *Escherichia coli* ATCC 610100, *Pseudomonas aeruginosa* ATCC 614000, *Haemophilus influenzae* A21515, *Staphylococcus aureus*, methicillin resistant (MRSA) ATCC 605000, *Enterococcus faecalis* ATCC 662000, *Streptococcus pneumoniae* ATCC 661100 and *Candida glabrata* ATCC 200918. All cultures were maintained in Brain Heart Infusion Medium (Oxoid), except *C. glabrata*, which was maintained in Potato Dextrose Broth (Difco).

For antimicrobial assays of *E. coli, P. aeruginosa, H. influenzae*, MRSA, *E. faecalis* and *S. pneumoniae*, the cells in Brain Heart Infusion Medium were added to 96 well plates at a volume of 176 µl/well. The compound to be tested was added to the wells (20 µl/well) together with 10 µl of 0.2 mg/ml resazurin (Sigma). The plates were incubated at 37° C. for 4 to 6 hours. The growth of the cultures was monitored by measuring the fluorescence of the plates using a fluorometer with $\lambda_{ex}$=535 nm and $\lambda_{em}$=590 nm filters. Resazurin dye without cells was used to determine the background, which was subtracted from the data for all experimental wells. The data were analyzed using Prism software (GraphPad Software). The data were normalized to the average of the cells treated with media only (100% cell growth) and the $IC_{50}$ values were determined using a standard sigmoidal dose response curve fitting algorithm.

For the antimicrobial assay of *C. glabrata*, the procedure was same as above except Potato Dextrose medium was used.

The results were as follows in Table 3:

TABLE 3

| Reported IC$_{50}$ values: | |
|---|---|
| E. coli | >4 µg/ml |
| P. aeruginosa | >4 µg/ml |
| H. influenzae | >4 µg/ml |
| MRSA | 1 µg/ml (2.2 uM) |
| E. faecalis | 3 µg/ml (6.6 uM) |
| S. Pneumoniae | 4 µg/ml (8.8 uM |
| C. glabrata | 3 µg/ml (6.6 uM) |

The anti-infective potential of the compound was re-evaluated in susceptibility assays performed by broth microdilution in accordance with National Committee for Clinical Laboratory Standards (NCCLS) guidelines, M7-A5, January 2000. The compound was tested versus the following microorganisms: *Staphylococcus aureus* (MSSA), *Staphylococcus aureus* (MRSA), *Streptococcus pneumoniae*, vancomycin-sensitive *Enterococcus faecalis, Haemophilus influenzae, Pseudomonas aeruginosa* and *Candida albicans*. As shown in Table 4, no significant anti-microbial activity was detected against any of the organisms.

TABLE 4

| Genus | Species | ID | MIC, µg/ml | MLC, µg/ml |
|---|---|---|---|---|
| Staphyloccus | aureus | MSSA | >32 | >32 |
| Staphyloccus | aureus | MRSA | 12 | >32 |
| Streptococcus | pneumoniae | 49619 | 32 | >32 |
| Enterococcus | faecalis | VSE | 32 | >32 |
| Escherichia | coli | imp | >32 | >32 |
| Haemophilus | influenzae | 49766 | >32 | >32 |
| Pseudomona | aeruginosa | 27853 | >32 | >32 |
| Candida | albicans | 90028 | >32 | >32 |

EXAMPLE 6

Pharmaceutical Formulations of the Macrocyclic Lactams

1) Formulations Administered Intravenously, by Drip, Injection, or The Like

Vials containing 5 g of powdered glucose are each added aseptically with 10 mg of a compound synthesized by the method of the invention and sealed. After being charged with nitrogen, helium or other inert gas, the vials are stored in a cool, dark place. Before use, the contents are dissolved in ethanol and added to 100 ml of a 0.85% physiological salt water solution. The resultant solution is administered as a method of inhibiting the growth of a cancerous tumor in a human diagnosed as having such a tumor at between approximately 10 ml/day to approximately 1000 ml/day, intravenously, by drip, or via a subcutaneous or intraperitoneal injection, as deemed appropriate by those of ordinary skill in the art.

2) Formulation to be Administered Orally Or The Like

A mixture obtained by thoroughly blending 1 g of a compound obtained and purified by the method of the invention, 98 g of lactose and 1 g of hydroxypropyl cellulose is formed into granules by any conventional method. The granules are thoroughly dried and sifted to obtain a granule preparation suitable for packaging in bottles or by heat sealing. The resultant granule preparations are orally administered at between approximately 100 ml/day to approximately 1000 ml/day, depending on the symptoms, as deemed appropriate by those of ordinary skill in the art of treating cancerous tumors in humans.

The examples described above are set forth solely to assist in the understanding of the invention. Thus, those skilled in the art will appreciate that the methods may provide derivatives of compounds.

One skilled in the art would readily appreciate that the present invention is well adapted to carry out the objects and obtain the ends and advantages mentioned, as well as those inherent therein. The methods and procedures described herein are presently representative of preferred embodiments and are exemplary and are not intended as limitations on the scope of the invention. Changes therein and other uses will occur to those skilled in the art which are encompassed within the spirit of the invention.

It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions indicates the exclusion of equivalents of the features shown and described or portions thereof. It is recognized that various modifications are possible within the scope of the invention. Thus, it should be understood that although the present invention has been specifically disclosed by preferred embodiments and optional features, modification and variation of the concepts herein disclosed may be resorted to by those skilled in the art, and that such modifications and variations are considered to be falling within the scope of the invention.

What is claimed is:

1. A substantially purified compound having the following structure:

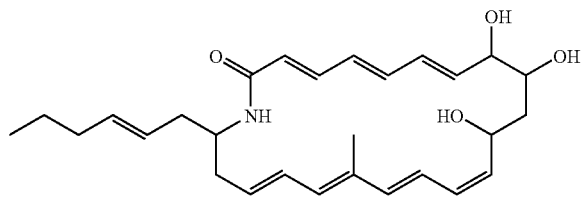

or its acid-addition salts or its pro-drug esters.

2. A method of treating an individual with cancer, comprising:
administering to the individual a compound of claim 1, its acid-addition salts or its pro-drug esters, wherein the cancer is selected from the group consisting of an adenocarcinoma colon cancer, a prostate cancer, a T-cell leukemia, and a melanoma cancer.

3. A method of treating cancer comprising the step of contacting a cancer cell with a compound of claim 1, wherein the cancer is selected from the group consisting of an adenocarcinoma colon cancer, a prostate cancer, a T-cell leukemia, and a melanoma cancer.

4. The method of claim 3, wherein the cancer is an adenocarcinoma colon cancer.

5. The method of claim 3, wherein the cancer is a prostate cancer.

6. The method of claim 3, wherein the cancer is a T-cell leukemia.

7. The method of claim 3, wherein the cancer is a melanoma cancer.

8. The method of claim 2, wherein the cancer is an adenocarcinoma colon cancer.

9. The method of claim 2, wherein the cancer is a prostate cancer.

10. The method of claim 2, wherein the cancer is a T-cell leukemia.

11. The method of claim 2, wherein the cancer is a melanoma cancer.

12. The method of claim 2, wherein the compound is administered with a pharmaceutically acceptable carrier, diluent, or excipient.

13. A method of treating an individual with cancer, comprising administering to the individual a composition comprising the compound of claim 1, an acid-addition salt thereof, or a pro-drug ester therof, wherein the cancer is selected from the group consisting of an adenocarcinoma colon cancer, a prostate cancer, a T-cell leukemia, and a melanoma cancer.

14. The method of claim 13, wherein the composition is administered with a pharmaceutically acceptable carrier, diluent, or excipient.

15. The method of claim 13, wherein the cancer is an adenocarcinoma colon cancer.

16. The method of claim 13, wherein the cancer is a prostate cancer.

17. The method of claim 13, wherein the cancer is a T-cell leukemia.

18. The method of claim 13, wherein the cancer is a melanoma cancer.

* * * * *